United States Patent [19]

Mistry

[11] Patent Number: 4,759,345

[45] Date of Patent: Jul. 26, 1988

[54] RADIATION SHIELDED SEED LOADER FOR HAND IMPLANTER HYPODERMIC NEEDLES APPARATUS AND METHOD

[76] Inventor: Vitthalbhai D. Mistry, 11306 Pradera Dr., Austin, Tex. 78759

[21] Appl. No.: 12,626

[22] Filed: Feb. 9, 1987

[51] Int. Cl.$^4$ .............................................. A61N 5/01
[52] U.S. Cl. .................................... 128/1.2; 250/507.1
[58] Field of Search .................................. 128/1.1–1.2; 250/506.1, 507.1; 604/60–61

[56] References Cited

U.S. PATENT DOCUMENTS

| | | | |
|---|---|---|---|
| 2,009,393 | 7/1935 | Failla | 604/60 |
| 2,269,963 | 1/1942 | Wappler | 604/61 |
| 2,857,524 | 10/1958 | Tabern et al. | 128/1.2 |
| 4,167,179 | 9/1979 | Kirsch | 128/1.2 |
| 4,241,728 | 12/1980 | Mirell | 128/1.1 |
| 4,357,541 | 11/1982 | Ernst | 250/507.1 |
| 4,382,512 | 5/1983 | Furminger | 250/507.1 X |
| 4,401,108 | 8/1983 | Galkin et al. | 128/1.1 |
| 4,497,349 | 2/1985 | Farley | 128/1.1 X |

Primary Examiner—William E. Kamm
Assistant Examiner—Angela D. Sykes
Attorney, Agent, or Firm—John Nevin Shaffer, Jr.

[57] ABSTRACT

A safe radiation shielded seed loader for hand implanter hypodermic needles with removable seed loading disk. The removable seed loading disk enhances the ability to quickly and safely load radioactive seeds into hypodermic needles. As a result, the loading process is greatly expedited and a substantial reduction of the radiation exposure time to hands, fingers and eyes of the person loading the seeds is accomplished. Once loaded, a spacer-key prevents obturators from pressing the loaded seeds, now carried in a shielded container, out of the needles until use. A removable carrying handle with lifting arms and a cover plate with a recessed area to accommodate the heads of the obturators is provided. As a result, the easily and quickly loaded device may be safely transported to the implantation site without fear of radiation exposure or damage to the needles themselves.

11 Claims, 2 Drawing Sheets

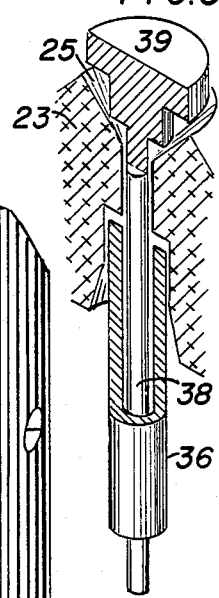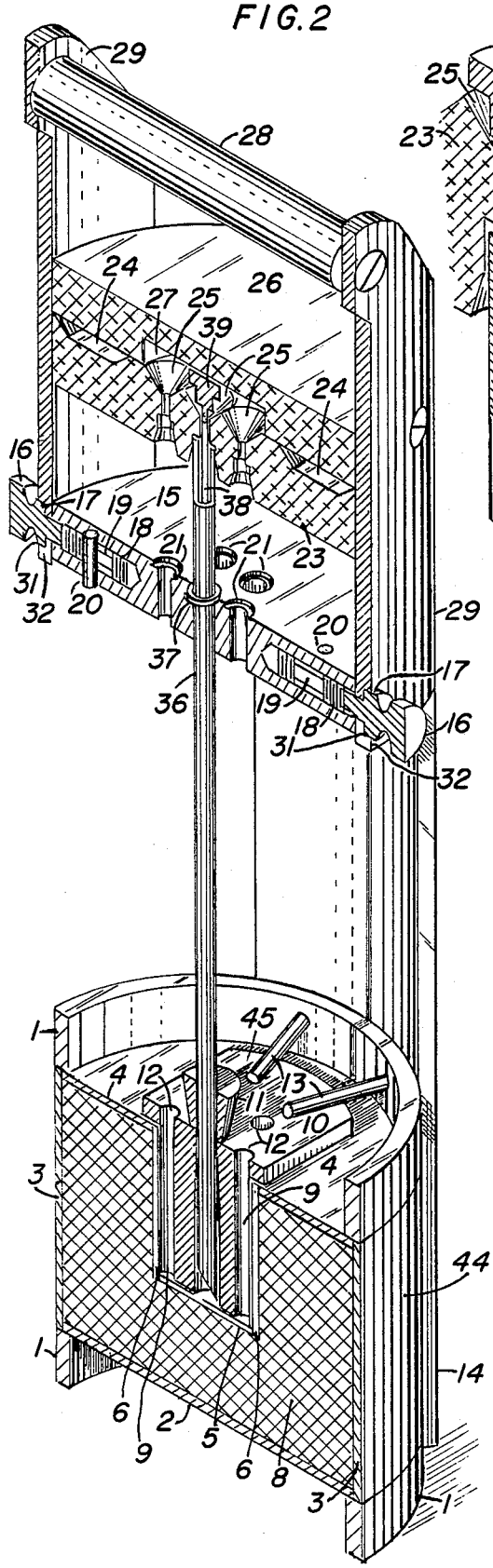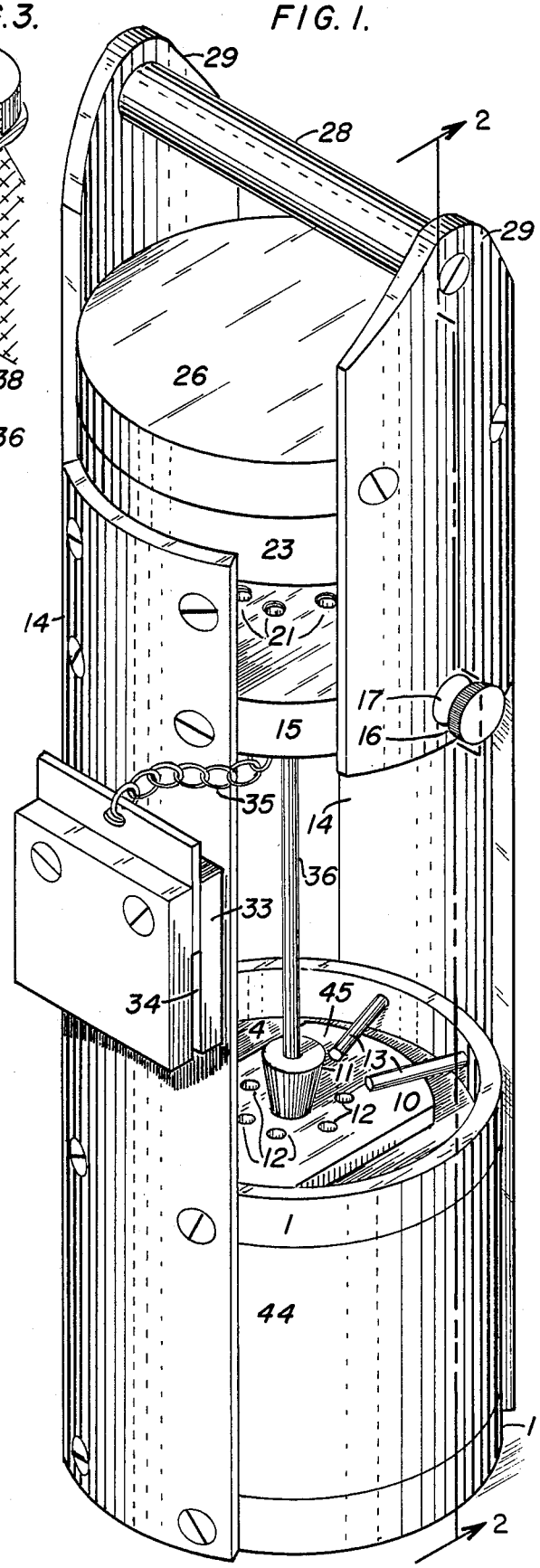

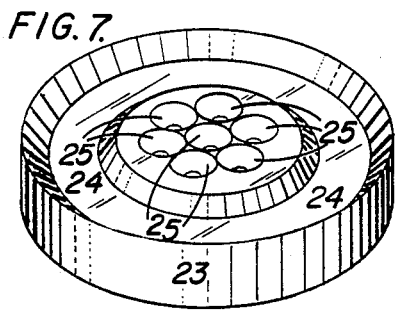
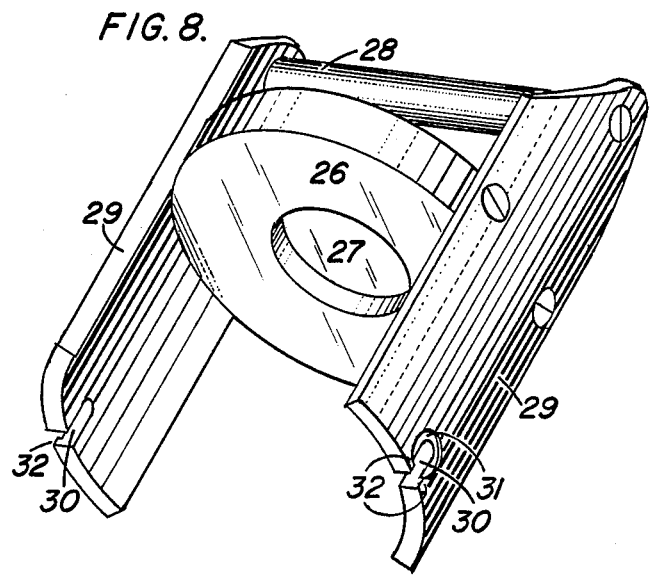
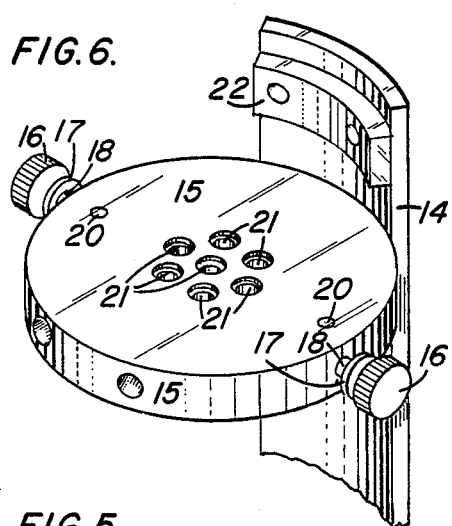
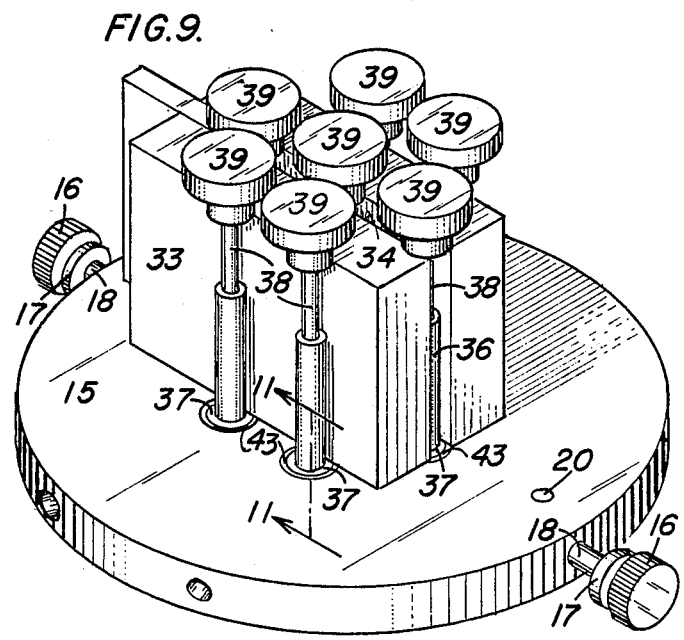
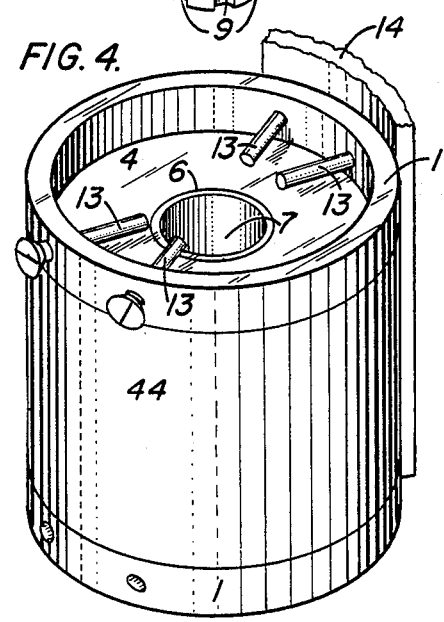
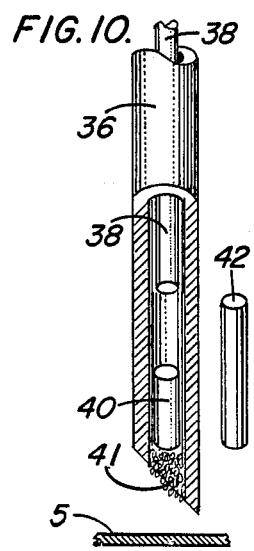
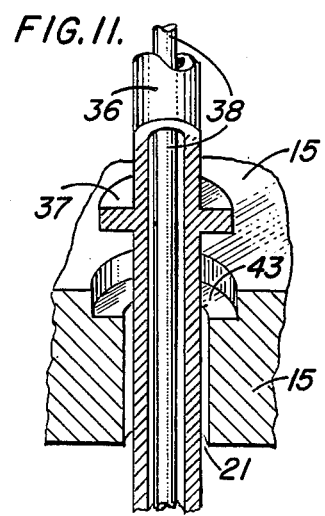

RADIATION SHIELDED SEED LOADER FOR HAND IMPLANTER HYPODERMIC NEEDLES APPARATUS AND METHOD

BACKGROUND OF THE INVENTION

This invention relates to an improved radiation shielded seed loader for hand implanter hypodermic needles. Hand implants are performed on small superficial tumors and nodules without using an implanting device except hand held hypodermic needles. Radioactive gold seeds and on rare occasion iodine seeds are used for the implants. This type of implant is mainly geared for patient who do not require hospitalization after the implant is performed. Local anesthetic is administered and the number of radioactive seeds implanted is limited by the size of the tumor, activity of each seed and most important, the exposure levels at one meter from the implanted area.

Devices for inserting radioactive seeds in and around tumors have been known in the art for several years. For example, hand held needles have been devised to handle radioactive seeds for insertion into tumors. An example of such a needle is disclosed in Failla U.S. Pat. No. 2,009,393 which utilizes a needle with a trough provided in the tip for accomplishing loading by placing the seed on a hard surface and pressing the needle over it. Repetitive insertion of radioactive seeds is provided by the Wappler U.S. Pat. No. 2,269,963. The Wappler patent discloses a pistol shaped grip attached to an injection means. Radioactive seeds may be implanted one after another by simply pulling the trigger of the device. Implantation of more than one radioactive seed at one time, all in one plane, is accomplished in Kirsch U.S. Pat. No. 4,167,179. Larger, more complicated devices utilizing electric circuits and multiple injection means have been disclosed. Such a device is disclosed in Chassagne et al., U.S. Pat. No. 3,861,380.

One major problem associated with handling of radioactive seeds is the radiation exposure to individuals who handle these seeds before and during the implantation. Existing methods of loading radioactive seeds in hand implanter hypodermic needles is very cumbersome and time consuming, leading to high exposure to hands, fingers and eyes of the person loading the seeds. Frequently, there exists radiation levels above normal limits in the area where the implant takes place. At some institutions such an implant is done in a spatially restricted area where the radioactive materials are stored as well as heavy L-shaped lead shielding is located for radiation protection during loading of the needles. At other institutions the heavy L-shaped lead shielding is transported to the room where implant takes place, so that it can be used as radiation protection device during loading of the needles.

In short, a drawback to devices for inserting radioactive seeds known in the art is that little or no attention is paid to the prevention or the shielding of the radiation emission while loading the hypodermic needles. A further drawback is that no safe, easy and quick means for loading hypodermic needles is provided. A still further drawback is that once one or more needles are loaded, no simple, portable, stable means for transporting the loaded radioactive needles is provided.

Thus, there is a need in the art for providing a radiation shielded seed loader for hand implanter hypodermic needles which significantly lessens the exposure levels of radiation to the hand, fingers and eyes of the person loading the seeds.

It, therefore, is an object of this invention to provide an improved, safe, system for loading hand implanter hypodermic needles with radioactive seeds in a manner that limits the exposure of an individual to radiation.

A further object of this invention is to expedite the loading process with an improved means for receiving radioactive seeds.

Still, another object of this invention is to provide a convenient, radiation shielded container to store loaded hypodermic needles so that radiation exposure levels are reduced in the implant area.

A further object is to provide a device capable of being sterilized by a variety of methods.

A further object of the invention is to make a shielded device that is light weight and secure, so that it is possible to transport it safely with the radioactive seeds in place, from loading area to the implant area, or even to a far away site.

Yet another object is to make the shielded device rigid so that needles remain well protected from any minor mechanical stress during transportation.

A further object is to provide stability to the device so that it does not topple over under minor accidental bumps.

A further object is to provide a device capable of preventing the plungers of hypodermic needles from accidentally pushing out the seeds during transportation.

SHORT STATEMENT OF THE INVENTION

Accordingly, an upright standing, cylindrically shaped, shielded base is provided. Two oppositely positioned support arms are attached to this base. The ends opposite from the shielded base are attached to an alignment disk. Needles whose tips are plugged with bone wax are inserted into holes drilled through the alignment disk with the tips lodged in a central removable piece which is held securely in position in the radioactive shielded base. A removable seed loading disk is placed over the tops of the empty needles. The loading disk is constructed so that the radioactive seeds are easily deposited into each individual needle and loose radioactive seeds are prevented from rolling away. Once the needles are loaded, the loading disk is removed and obturators or plungers are inserted into the tops of the needles. The spacer-key is then inserted to hold the loaded needles securely in place and to prevent the plungers from pushing the seeds through bone wax that is used to plug the tips of the needles until such time as the needles are used. Once the spacer-key is in place a cover plate with a recessed area in its underside to accommodate the cylindrical heads of the obturators is placed over the spacer key. The cover plate has a carrying handle attached to two lifting arms which also keep the spacer-key from sliding out. The two lifting arms are designed to be removably attached to the alignment disk. The separate parts of the device, other than the radioactive shielded base, which is filled with lead or some other radiation attenuating material, are made of light weight materials such as aluminum and/or stainless steel. This imbues the device with the ability to resist toppling over due to minor accidental bumps because it is designed to have most of its weight in the base. Additionally, this construction enables the device to be sterilized easily by a variety of methods without damage to the device.

As a result of this unique construction, the loading of radioactive seeds is improved so that radiation exposure levels to an individual's hands, fingers and eyes are significantly reduced. Additionally, this invention significantly expedites the loading process thereby substantially reducing the exposure time to hands, fingers and eyes of the person loading the seeds. Once loaded, it is possible to transport the device safely with radioactive seeds in place and shielded. Furthermore this device reduces radiation exposure levels in the implantation area from the loaded needles. The high strength, light weight construction of the device ensures that the needles themselves are protected from any minor mechanical stress during transportation. Additionally, the device is designed so that the plungers of the hypodermic needles are prevented from accidentally pushing out the seeds during transportation.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a perspective view of a preferred embodiment of the present invention, the radiation shielded seed loader for hand implanter hypodermic needles as it appears when completely assembled for storage;

FIG. 2 is a section view taken along the lines of 2—2 of FIG. 1;

FIG. 3 is a magnified view of a section of the loading disk showing the needle and an obturator or a plunger;

FIG. 4 is a perspective view of the shielded container base sandwiched between two collar rings;

FIG. 5 is a perspective view of the removable central piece designed to be inserted into the well of the shielded container;

FIG. 6 is a perspective view of the needle alignment disk with two thumb screws attached on one of the support arms shown partially cut;

FIG. 7 is a perspective view of the seed loading disk;

FIG. 8 is a perspective view of the cover plate with carrying handle;

FIG. 9 is a magnified perspective view of the spacer key in place after all the needles have been loaded;

FIG. 10 is a magnified sectional view of the tip of a loaded needle showing bone wax, the radioactive seed and the relative location of the tip of the obturator when the spacer key is in place; and FIG. 11 is a magnified sectional view taken along lines 11—11 of FIG. 9 of the alignment disk 15 with needle in place.

DETAILED DESCRIPTION OF THE PREFERRED EMBODIMENT

The preferred embodiment of the present invention is illustrated by way of example in FIGS. 1-11. It is to be noted that the hypodermic needle and the obturator are not a part of this invention and that they are shown in the drawings for the purposes of clarity only. With specific reference to FIGS. 1 and 2, a shielded seed loader includes shielded container 44, comprised of two collar rings 1 and a stainless steel case, composed of sides 2, 3, 4, 5 and 6. Within the stainless steel case is formed a well 7 (see FIG. 4) of shielded container 44. A removable central piece 45, made of stainless steel, resides within this well 7. The interior of shielded container 44 contains a metal 8, such as lead. Two oppositely positioned support arms 14 are attached at their lower ends to the upper and lower collar rings 1 sandwiching the shielded container 44. At short length below their upper ends, support arms 14 are attached to and securely hold in place needle alignment disk 15. Needle alignment disk 15 has two oppositely positioned thumb screws 16 each with thumb screw lips 17 and thumb screw stems 18. There are recessed shaved portions 19 of thumb screws 16 within which fit retaining pins 20. Needle alignment disk 15 has a plurality of needle holes 21 drilled there-through.

As shown in the section view presented by FIG. 2, more fully disclosed in FIG. 7, is the seed loading disk 23, which has a plurality of funnel holes 25.

FIGS. 1 and 9 illustrate spacer-key 33 connected by chain 35 to the inside of one of the support arms 14. Spacer-key 33 has needle slot 34 extending partially in the longitudinal direction through spacer-key 33.

Hypodermic needle 36, (which is not a part of this invention) as illustrated in FIGS. 1, 2, 3, 9, 10 and 11, has collar 37 and is constructed so as to have a hollow interior that just receives obturator 38 with a flat cylindrical head 39.

FIG. 10 illustrates the relative size of radioactive gold seed 40 and the iodine seed 42 which, typically, is almost twice as big. FIG. 10 also demonstrates the use of sterile bone wax 41 to temporarily plug the tip of needle 36.

FIG. 1 then, is a perspective drawing of the invention as it would appear when completely assembled for storage. Spacer-key 33, which normally hangs on a chain 35 on the inner side of support arm 14, is shown outside the device for purposes of clarity.

FIG. 2 further illustrates the construction of the two thumb screws 16. Thumb screws 16, located in needle alignment disk 15, are kept from being screwed completely out of alignment disk 15 by means of retaining pins 20. Each retaining pin 20 is placed within the recessed shaved portion 19 of thumb screws 16. The recessed shaved portions 19 of thumb screws 16 span the travel of thumb screw 16 before it is stopped by the retaining pin 20 coming in contact with the unshaved threaded portion of thumb screw 16. As a result, thumb screws 16 are prevented from being completely unscrewed and lost.

FIG. 3 is a magnified view of the section of the seed loading disk 23 through a funnel hole 25 which can be seen to take varying shapes from the top of seed loading disk 23 to the bottom of seed loading disk 23. This figure shows how a needle 36 and an obturator 38 can be fitted together within the disk 23 when the device is assembled for storage. Funnel hole 25 narrows to provide a hole just large enough to pass the obturator 38 and the radioactive seeds 40, but small enough not to pass needle 36, which is held in place in a larger portion of funnel hole 25 below. This construction helps the seed to fall through into needle 36 and land onto bone wax 41 at the tip without getting caught elsewhere.

FIG. 4 shows shielded container 44 held between two collar rings 1, fixed onto two support arms 14. Four retaining pins 13, two of which are on the right hand side and the other two of which are on the left hand side, are long screws whose threads are shaved off part way, pass through support arm 14 and screw into upper ring 1 and extend above the top floor of shielded container 44. The lower portion of the device, as shown in FIG. 4, is a shielded container 44 made of lead metal 8 completely encapsulated within a stainless steel case composed of sections 2, 3, 4, 5 and 6, so as to prevent lead contamination. It is to be understood that any material (for example tungsten) with similar or better attenuation properties to gamma rays can be used instead of lead metal, but lead is preferred for its easy availability and high density. For mechanical stability, light weight metal, like aluminum, is used for the construction of the seed loading disk 23, the two support arms 14, the needle alignment disk 15, the spacer-key 33 and carrying handle 28 with cover plate 26. Other types of material with similar stress properties can also be used in place of aluminum. Nonetheless, aluminum is preferred over stainless steel because of its lighter density, easy availability and cost effectiveness. Also, during steam sterilization, for instance, thermal expansion of different materials can cause weakening of joints of a structure. This preferred construction avoids this problem.

FIG. 5 shows removable central piece 45, which is made of stainless steel. Removable central piece 45 consists of a handle 11, a flange 10 and a core with a central hole passing through handle 11 and six longitudinal grooves 9 on the periphery corresponding to the six holes 12 on the flange 10. The flange 10, is shown in its proper orientation to clear the retaining pins 13, shown in FIGURE 4, when it is first inserted in the well 7 of shielded container 44. FIG. 1 shows flange 10 as rotated underneath retaining pins 13 and secured in its proper position thereby.

FIG. 6 illustrates needle alignment disk 15 with two thumb screws 16 and their retaining pins 20. Also illustrated in FIG. 6 is one of two oppositely positioned seed loading disk supports 22. One each is affixed to the inside of upmost portion of support arms 14.

FIG. 7 shows a seed loading disk 23 which has an annular trough 24 and a plurality of funnel holes 25 matching those holes 21 in alignment disk 15.

FIG. 8 shows cover plate 26 connected to two oppositely positioned lifting arms 29, to which is also attached carrying handle 28. Recessed area 27 in cover plate 26 is provided in the bottom side of cover plate 26. On the lower ends of lifting arms 29 are two oppositely positioned thumb screw retaining slots 30. The thumb screw retaining slots 30 have wide recessed portions 31 and ridges 32 all designed to admit thumb screw stems 18 and to lodge thumb screw lips 17.

FIG. 9 is a magnified perspective view of the spacer-key 33 in place after all the needles 36 are loaded. Spacer-key 33 has a longitudinal slot 34 located in the middle which is designed to accommodate three of the centrally located needles 36. FIG. 9 illustrates clearly how spacer-key 33 lodges between collar 37 of all the needles 36 and the lower portions of the heads 39 of obturators 38, thereby preventing the obturators 38 from being pressed totally down into needles 36 and ejecting the seeds in the well 7.

FIG. 10 is a magnified sectional view of the tip of a loaded needle 36 showing sterile bone wax 41, the radioactive gold seed 40 and the relative location of the tip of the obturator or plunger 38 when the spacer-key 33 is in place. It should be noted, as shown in this figure, that there is space for one more gold seed 40 if desired. If an iodine seed 42 is used instead of gold seed 40, then only one seed 42 can be accommodated because of its greater length.

FIG. 11 is a magnified sectional view of alignment disk 15 through hole 21. This figure illustrates how collar 37 of hypodermic needle 36 fits into a recessed portion 43 of hole 21 thereby enabling spacer-key 33 to slide easily across the top of alignment disk 15.

Prior to utilization of the device, it is first sterilized using any method known in the art such as gas, liquid or steam. It is convenient to steam sterilize or autoclave this device. During sterilization the device is disassembled into four pieces, namely the carrying handle 28 with cover plate 26, the seed loading disk 23, the removable central piece 45, and the rest of the device which is a permanently assembled unit consisting primarily of the shielded container 44, the two support arms 14, needle alignment disk 15 and spacer-key 33 hanging on chain 35.

Once sterilized, the sterilized pieces of the device are assembled and then used for loading seeds 40 or 42 in the following sequence. First, the core of the removable central piece 45 is inserted into the well 7 of shielded container 44 by grasping handle 11 with the thumb and the index finger and orienting the narrow portion of flange 10 to clear retaining pins 13 (see FIGS. 4 and 5).

Once the narrow portion of flange 10 clears retaining pins 13, central piece 45 is lowered and rotated through 90 degrees so that the longer portion of flange 10 lodges under and is secured in position by the four retaining pins 13 as shown in FIG. 1. This orientation of central piece 45, together with a minimum of two needles 36 in place, prevents the central piece 45 from being dislodged and sliding out of well 7 during transportation of the device. As a result, radioactive seeds 40 or 42 remain shielded within shielded container 44 during transportation.

Once central piece 45 is in place in shielded container 44 with proper orientation of its flange 10, as discussed above, the device is ready for insertion of hypodermic needles 36. Prior to utilization, the sharp end of each needle 36 is plugged with a tiny amount of sterile bone wax 41. This is done by scraping needle 36 in bone wax stock so that approximately 2 millimeters of the needle 36 tip is plugged with bone wax 41. Bone wax 41 prevents radioactive seeds 40 from dropping out of needle 36 into well 7 of shielded container 44. Excess wax 41 sticking on the outside of the sharp end of the needle 36 is simply wiped off with sterile paper or sterile cloth. After this procedure, the sharp end of needle 36, plugged with sterile bone wax 41, is inserted through one of a number of holes 21, seven in these illustrations, in alignment disk 15 and carefully directed into a corresponding hole 12 in the flange of removable central piece 45. In this embodiment, a maximum of seven needles 36 can thus be made ready and inserted into the holes of alignment disk 15. It is not necessary to prepare all seven needles 36 if less than seven seeds 40 or 42 are to be implanted. Nonetheless, it is clear that alignment disk 15 and central piece 45 hold the needles in proper orientation for quicker loading of seeds 40 or 42.

Once the needles 36 are in place, seed loading disk 23 is placed over the blunt open ends of needles 36, such that the trough 24 and the conical depressions or funnel holes 25 of loading disk 23 face upward. Seed loading disk 23 is gently rotated until it drops in place over the blunt open ends of needles 36 and comes to rest on the two disk supports 22. If fewer than seven needles 36 are to be loaded, obturators or plungers 38 may be inserted, as a precautionary measure against dropping seeds into those funnel holes 25 under which there are no needles 36. At this point, the device, with the needles in place, but without cover plate 26, is placed, preferably, behind an L-shaped shielding block of ordinary design known in the art. The container of radioactive seeds 40 or 42 is also kept behind this L-shaped shielding block. The loading procedure proceeds thusly. Using long forceps (not shown), seeds 40 or 42 are picked up and carefully dropped, one at a time, into each funnel hole 25 under which a needle 36 is located. The trough 24 of seed loading disk 23 catches any seed 40 or 42 that may accidentally roll away or be dropped due to lost grip during the process of loading them into funnel holes 25 of seed loading disk 23. It is a common practice to load only one seed 40 per needle 36 for hand implants. Because of the shielding constraint and the physical size of seed 40, loading per needle is restricted to a maximum of two gold seeds 40 and only one iodine seed 42 per needle 36.

Now, the seed loading disk 23, together with any protective obturators 38 in place, is lifted off the blunt open ends of the loaded needles 36 and placed aside to be used if and when needed again. Then a plunger or obturator 38 is partially inserted into each loaded needle 36 from the blunt end so that at least a half of an inch of travel is still left in the needle 36. This precaution of partial insertion of an obturator 38 prevents a seed 40 or 42 from being pushed out from the sharp end of needle 36. This completes the loading of the needles 36 with radioactive seeds 40 or 42. It is now, at this stage, safe to remove the device with the loaded needles from behind the L-shaped shielding block.

After the necessary number of plungers 38 are partially inserted, the spacer-key 33 is slid into place as shown in FIG. 9. A line joining the two thumb screws 16 is the direction in which the spacer-key slot 34 is aligned before sliding the spacer-key 33 in place. The spacer-key 33 keeps enough space between the tip of the needle 36 and the tip of its obturator 38 to accommodate bone wax 41 and two gold seeds 40 or one iodine seed 42. Spacer-key 33 also prevents obturators 38 from being pressed accidentally and pushing the seed 40 or 42 out of needles 36 during transportation. A minimum of two needles 36, separated by a maximum distance between them in the direction of the line joining two thumb screws 16, are required for the spacer-key 33 to stay in place. The cover plate 26 with carrying handle 28 is then gently lowered over the obturator heads 39 thereby pushing them to their final preparatory stage as illustrated in FIG. 9. The spacer-key 33 is held in position when cover plate 26 with carrying handle 28 is secured to the device by means of two thumb screws 16.

Transportation of loaded needles 36 to the implant area is accomplished by securely attaching carrying handle 28 with cover plate 26 to needle alignment disk 15 by means of thumb screws 16. The two lifting arms 29 of the carrying handle 28 have slots 30 for admitting the stems 18 of thumb screws 16. Each slot 30 terminates in a wide and recessed portion 31 for each of the lips 17 of the two thumb screws 16 to be engaged in. Ridge 32 of the lifting arms 29 together with the engaged thumb screw lips 17, secures the carrying handle 28 on the alignment disk 15. The device, without the loading disk 23, but with spacer-key 33 and with cover plate 26 with carrying handle 28 in place, is secure enough to be transported to the implant room or any faraway site.

In the implant room, the cover plate 26 with handle 28 is removed by first unscrewing the thumb screws 16 and the spacer-key 33 is then carefully slid out. The needles 36 are then ready to be used for implantation of seeds 40 or 42.

It is obvious and apparent that this invention can be made in any shape with as large a shielded container as needed to hold as many needles as desirable. However, it is emphasized that the total activity of the radioactive seeds is limited by the fact that most of the implants are superficial and therefore a shielded container holding seven needles, as illustrated in this preferred embodiment, is a large enough number for most practical purposes and applications.

While the present invention has been disclosed in connection with the preferred embodiment thereof, it should be understood that there may be other embodiments which fall within the spirit and scope of the invention as defined in the following claims.

What is claimed is:

1. A radiation shielded seed loader for hand implanter hypodermic needles comprising:
   (A) a means for radiation attenuation;
   (B) a means for supporting and lifting said radiation attenuation means attached to said radiation attenuation means;
   (C) a means for aligning needles positioned over said radiation attenuation means;
   (D) a removable seed loading means with a plurality of funnel holes for dropping in radioactive seed means;
   (E) a well means in said radiation attenuation means for receiving needle tips loaded with said radioactive seed means so that said tips of said needles, once loaded with said radioactive seed means, are surrounded and shielded by said radiation attenuation means; and
   (F) a removably attachable means, with handle, for covering and protecting tops of said needles during transportation of said needles.

2. A radiation shielded seed loader for hand implanter hypodermic needles comprising:
   (A) a radiation shielded container base;
   (B) a pair of oppositely positioned support arms attached to two collar rings sandwiching said shielded container base;
   (C) a needle alignment disk attached to said support arms near an upper end of said support arms, positioned so that said alignment disk is directly over said shielded container base;
   (D) a removable radioactive seed loading disk for use in rapidly loading radioactive seeds into hypodermic needles in said alignment disk;
   (E) a well in said shielded container so that tips of said needles, once loaded with said radioactive seeds, are surrounded and shielded by said radiation shielded container base; and
   (F) a removably attachable cover plate, with handle, for covering and protecting tops of said needles and for transporting said needles.

3. The radiation shielded seed loader of claim 2 wherein said radiation shielded container base comprises:
   (A) a hollow unitary shielding case with a top and bottom;
   (B) a radiation attenuating material completely filling said shielding case;
   (C) upper and lower collars placed on to said top and under said bottom of said shielding case so that said shielding case is supported off the ground by said lower collar and so that an upper lip extending above said top of said shielding case is provided by said upper collar; and (D) two pairs of oppositely positioned retaining pins passing through and secured to said support arms and said upper collar so that free ends of said retaining pins extend inwardly towards said well, some distance above said top of said shielding case.

4. The radioactive shielded seed loader of claim 3 wherein said support arms further comprise:
(A) two pairs of supports attached to the inside of said support arms for supporting said removable seed loading disk.

5. The radioactive shielded seed loader of claim 4 wherein said needle alignment disk comprises:
(A) a plurality of spaced holes in said alignment disk through which shafts of said hypodermic needles are passed; and
(B) a pair of oppositely positioned cover plate retaining means attached to sided of said alignment disk which screw out from said disk so as to allow said cover plate to be fitted over stems of said retaining means and, when said retaining means are screwed into said disk, said cover plate is clamped securely to said side of said alignment disk thereby enabling a user to lift said container base by said handle.

6. The radiation shielded seed loader of claim 5 wherein said removable radioactive seed loading disk comprises:
(A) a plurality of spaced funnel holes in said loading disk, that just conform to said holes in said alignment disk, with wide sloped openings; and
(B) an annular trough surrounding said funnel holes so that misplaced radioactive seeds are retained on top of said loading disk.

7. The radiation shielded seed loader of claim 6 wherein said removably attachable cover plate comprises:
(A) a pair of oppositely positioned lifting arms joined at one end by said handle;
(B) said cover plate, attached to said lifting arms, with a recessed area conformed to admit heads of obturators, placed within said needles, without pressing down on said heads;
(C) receiving slots at another end of said lifting arms conformed so as just to admit stems of said retaining means and engage lips of said retaining means onto a corresponding recessed portion, with ridges, of said receiving slots of said lifting arms.

8. The radiation shielded seed loader of claim 7 further comprising a removable tip securing means wherein said tip securing means comprises:
(A) a downwardly extending shaft with longitudinal grooves conformed to said plurality of said funnel and alignment disk holes;
(B) a transverse flange, attached to the top of said shaft with holes conformed to said grooves, that, once said shaft of said tip centering means is placed within said well, just fits between said two pairs of retaining pins and comes to rest on top of said shielding case; and
(C) an upwardly extending handle attached to said flange so that said flange, once at rest on top of said shielding case, may be rotated beneath, and held in place by, said retaining pins.

9. The radiation shielded seed loader of claim 8 further comprising a spacer-key means wherein said spacer-key means comprises:
(A) a removable spacer-key, with a longitudinal slot, shaped in width so as to just pass between outer needles in said holes while inner needles in said holes just fit within said slot and shaped in height so that lower portions of said tops of said obturators just fit on top of, and are supported by, said spacer-key and are prevented from being pushed into said needles; and
(B) a connecting means connecting said spacer-key to the inside of one of said support arms.

10. A radiation shielded seed loader for hand implanter hypodermic needles comprising:
(A) a radiation shielded container base with a hollow unitary shielding case with a top and bottom;
(B) a radiation attenuating material completely filling said shielding case;
(C) upper and lower collars placed on to said top and under said bottom of said shielding case so that said shielding case is supported off the ground by said lower collar and so that an upper lip extending above said top of said shielding case is provided by said upper collar;
(D) a pair of oppositely positioned support arms attached to two collar rings sandwiching said shielded container base;
(E) two pair of oppositely positioned retaining pins passing through, and secured to, said support arms and said upper collar so that free ends of said retaining pins extend inwardly and some distance above said top of said shielding case;
(F) a needle alignment disk attached to said support arms near the upper ends of said support arms, positioned so that said alignment disk is directly over said shielded container base;
(G) a plurality of spaced holes in said alignment disk through which shafts of said hypodermic needles are passed;
(H) a removable radioactive seed loading disk for use in rapidly loading radioactive seeds into hypodermic needles in said alignment disk;
(I) a plurality of spaced funnel holes in said loading disk, that just conform to said holes in said alignment disk, with wide sloped openings;
(J) an annular trough surrounding said funnel holes so that misplaced radioactive seeds are retained on top of said loading disk;
(K) a well in said shielded container so that tips of said needles, once loaded with said radioactive seeds, are surrounded and shielded by said radiation shielded container base;
(L) a removably attachable cover plate, with handle, for covering and protecting tops of said needles and for transporting said needles within said shielded container;
(M) a pair of oppositely positioned lifting arms joined at one end by said handle;
(N) said cover plate, attached to said lifting arms, with a recessed area conformed to admit heads of obturators, placed within said needles, without pressing down on said heads;
(O) a pair of oppositely positioned cover plate retaining means attached to sides of said alignment disk which screw out from said disk so as to allow said cover plate to be fitted over stems of said retaining means and, when said retaining means are screwed into said disk, said cover plate is clamped securely to said alignment disk thereby enabling a user to lift said container base by said handle;
(P) receiving slots at another end of said lifting arms conformed so as just to admit stems of said retaining means and engage lips of said retaining means into a corresponding recessed portion, with ridges, of said receiving slots of said lifting arms;

(Q) a removable tip securing means with a downwardly extending shaft and with longitudinal grooves conformed to said plurality of said funnel and alignment disk holes;

(R) a transverse flange, attached to the top of said shaft with holes conformed to said grooves, that, once said shaft of said tip centering means is placed within said well, just fits between said two pairs of retaining pins and comes to rest on top of said shielding case;

(S) an upwardly extending handle attached to said flange so that said flange, once at rest on top of said shielding case, may be rotated beneath, and held in place by, said retaining pins;

(T) a removable spacer-key, with a longitudinal slot, shaped in width so as to just pass between outer needles in said holes while inner needles in said holes just fit within said slot and shaped in height so that lower portions of said tops of said obturators just fit on top of, and are supported by, said spacer-key and are prevented from being pushed into said needles; and (U) a connecting means connecting said spacer-key to the inside of one of said support arms.

11. A method of providing for a radioactive shielded seed loader for hand implanter hypodermic needles comprising the steps of:

(A) constructing a radiation shielded container base;

(B) attaching a pair of oppositely positioned support arms to two collar rings sandwiching said shielded container base;

(C) attaching a needle alignment disk to said support arms near an upper end of said support arms, positioned so that said alignment disk is directly over said shielded container base;

(D) locating a removable radioactive seed loading disk, for use in rapidly loading radioactive seeds into hypodermic needles in said alignment disk, directly over said needles in said alignment disk;

(E) plugging the tips of said needles;

(F) loading radioactive seeds into funnel holes in said radioactive seed loading disk so that radioactive seeds are placed in said tips of said needles;

(G) constructing a well in said shielded container base so that said tips of said needles, once loaded with said radioactive seeds, are surrounded and shielded by said radiation shielded container base;

(H) lowering a removable central piece in a well of the said shielded container base so that said tips of said needles are secured before loading said radioactive seeds;

(I) removing said radioactive seed loading disk and partially inserting obturators in said needles to restrict the location of said seeds in said tips of said needles within said shielded container base;

(J) sliding in a spacer-key so as to prevent said obturators from being pressed totally down into said needles, thereby pushing said seeds into said well of said shielded container base; and (K) attaching a removably attachable cover plate, with handle, for covering and protecting the tops of said needles and for transporting said needles within said shielded container.

* * * * *